United States Patent [19]
Lerk et al.

[11] Patent Number: 5,301,666
[45] Date of Patent: Apr. 12, 1994

[54] POWDER INHALER

[75] Inventors: Coenraad Lerk, Peize; Anne H. de Boer, Darchten, both of Netherlands

[73] Assignee: Asta Medica Aktiengesellschaft, Fed. Rep. of Germany

[21] Appl. No.: 992,250

[22] Filed: Dec. 14, 1992

[30] Foreign Application Priority Data

Dec. 14, 1991 [DE] Fed. Rep. of Germany ....... 4141363
Apr. 6, 1992 [DE] Fed. Rep. of Germany ....... 4211475

[51] Int. Cl.5 ...................... A61M 15/00; B65D 83/04
[52] U.S. Cl. .......................... 128/203.15; 128/203.21; 222/142.6
[58] Field of Search ...................... 128/203.15, 203.12, 128/203.21, 203.23, 203.24; 222/136, 138, 142.6, 335, 378, 379, 398, 399, 630

[56] References Cited

U.S. PATENT DOCUMENTS

| | | | |
|---|---|---|---|
| 1,216,252 | 2/1917 | Ferguson | 222/142.6 |
| 1,585,466 | 5/1926 | Coles | 128/203.24 |
| 3,096,910 | 7/1963 | Pehr | 222/142.6 X |
| 4,583,667 | 4/1986 | Fishman | 222/142.6 |
| 5,048,514 | 9/1991 | Ramella | 128/203.21 |
| 5,207,217 | 5/1993 | Cocozza | 128/203.21 |

FOREIGN PATENT DOCUMENTS

| | | | |
|---|---|---|---|
| 2041763 | 9/1980 | United Kingdom | 128/203.15 |
| 9113646 | 9/1991 | World Int. Prop. O. | 128/203.15 |
| 9203175 | 3/1992 | World Int. Prop. O. | 128/203.15 |
| 9205824 | 4/1992 | World Int. Prop. O. | 128/203.15 |

*Primary Examiner*—Edgar S. Burr
*Assistant Examiner*—Eric P. Raciti
*Attorney, Agent, or Firm*—Cushman, Darby & Cushman

[57] ABSTRACT

A powder inhaler for medication, for example for treatment of asthma. The inhaler has a rotatable and/or displaceable active substance magazine which has several apertures for medication. The magazine is moved with the aid of a control curve mechanism by rotation and/or displacement in such a manner that a chamber prefilled with active substance mixture is always located in front of the air inlet opening. The respiratory air stream of the patient is guided through the apparatus in such a manner that the air stream empties the chamber with the active substance mixture. The active substance mixture is divided up into respirable particles in a cyclone chamber or against an impact plate and then surrounded with a jacket stream of pure air and inhaled.

15 Claims, 18 Drawing Sheets

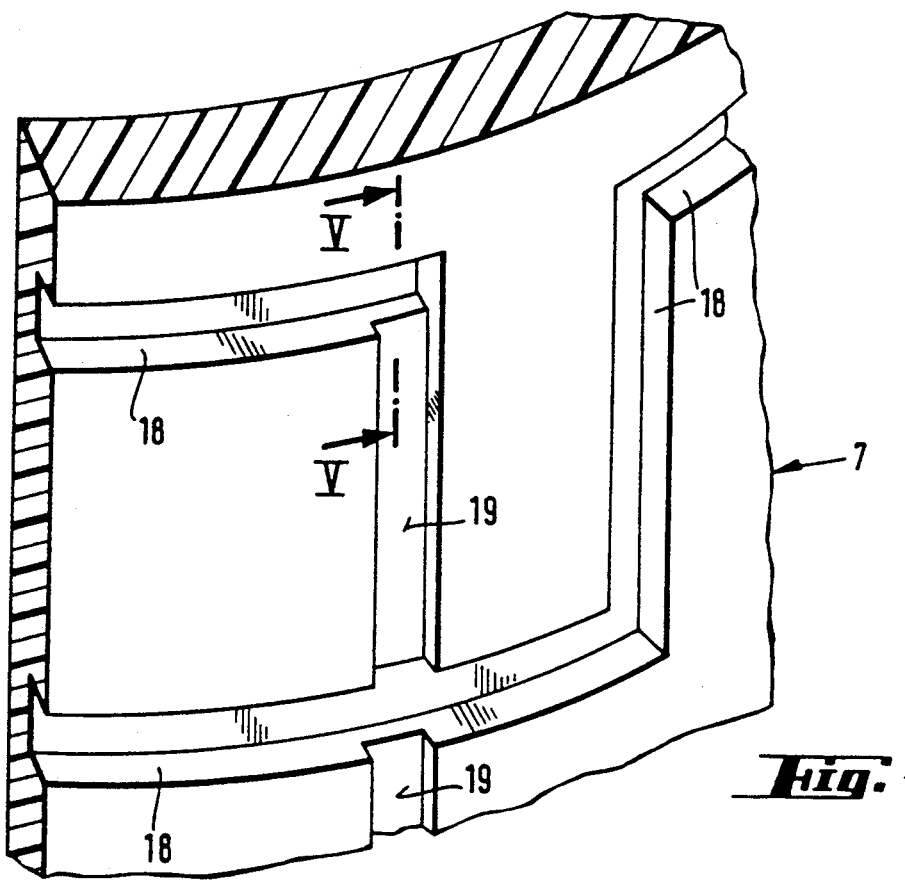
_Fig. 4_
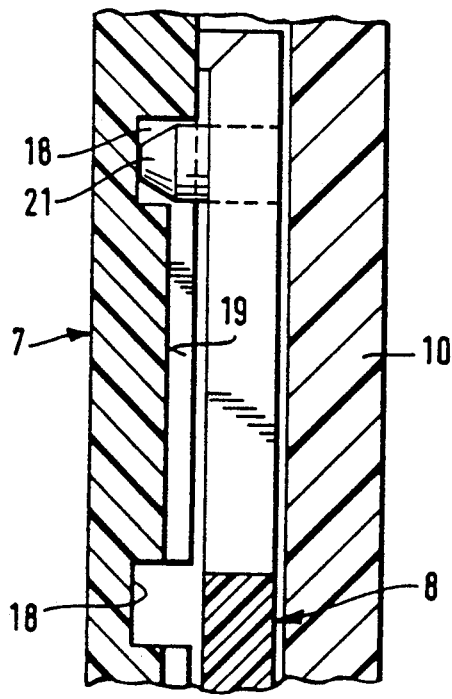
_Fig. 5A_
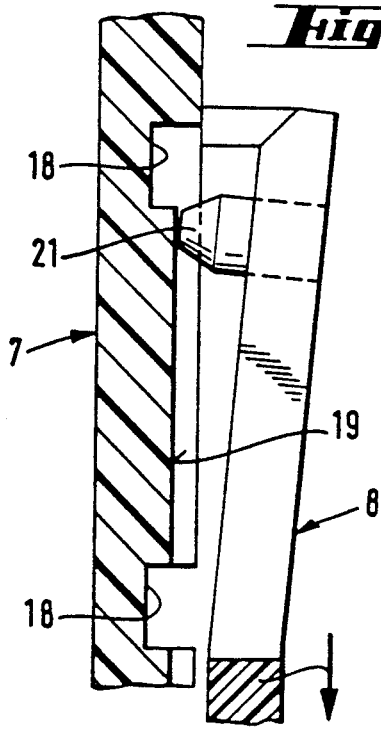
_Fig. 5B_

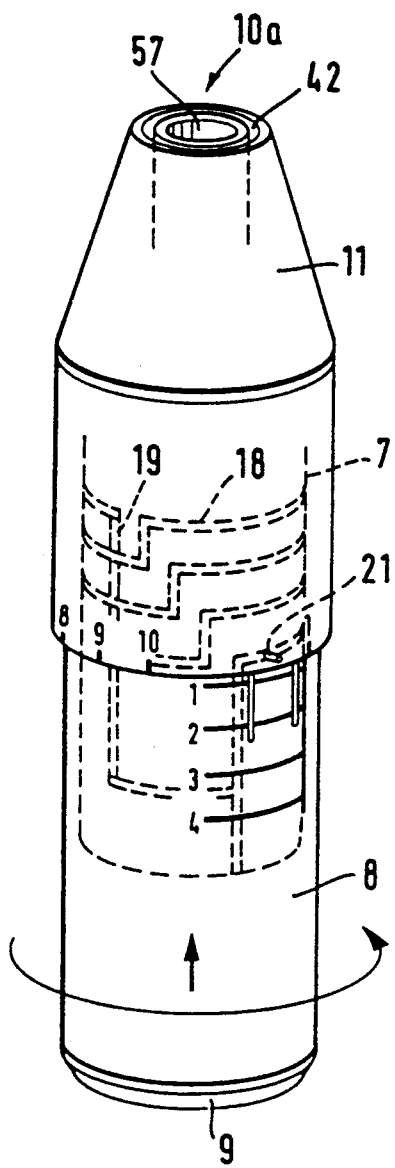
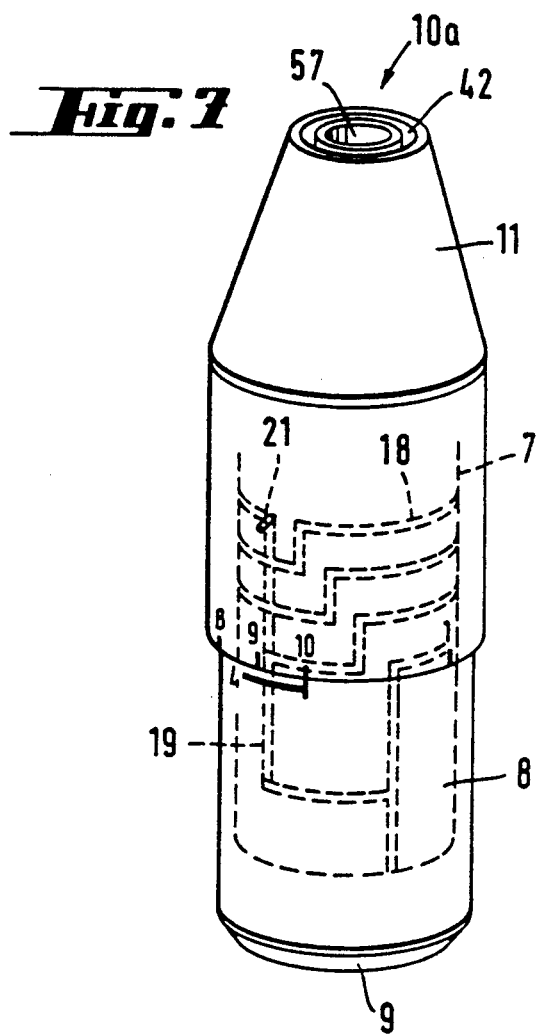
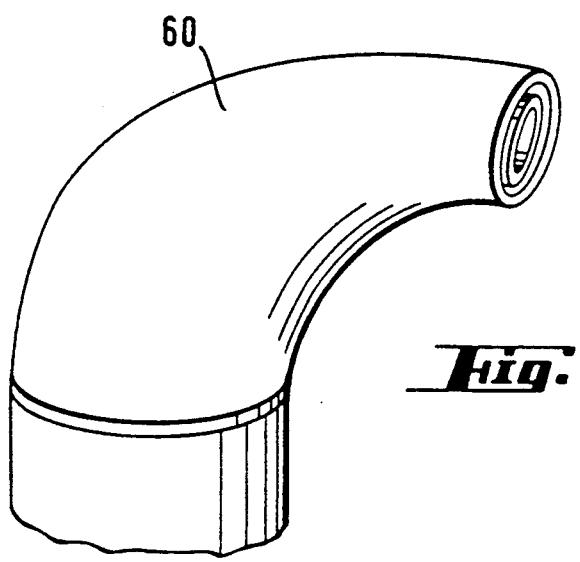

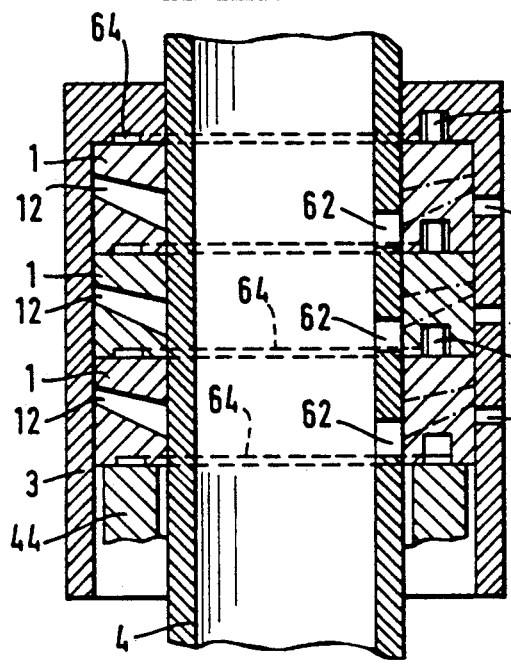
Fig. 14·A
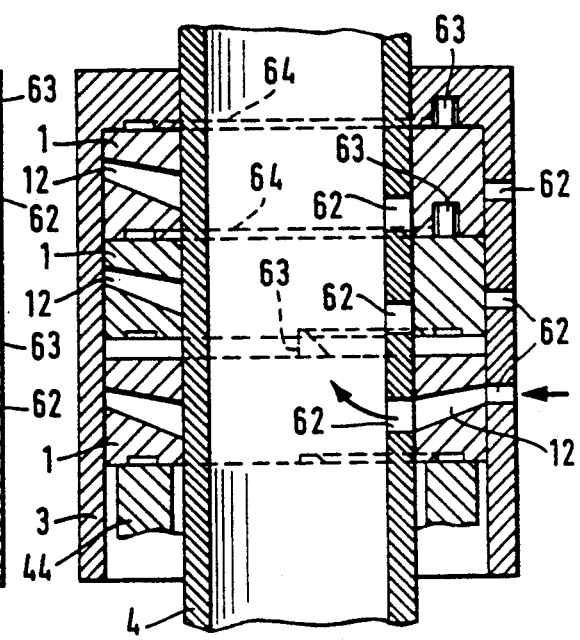
Fig. 14·B
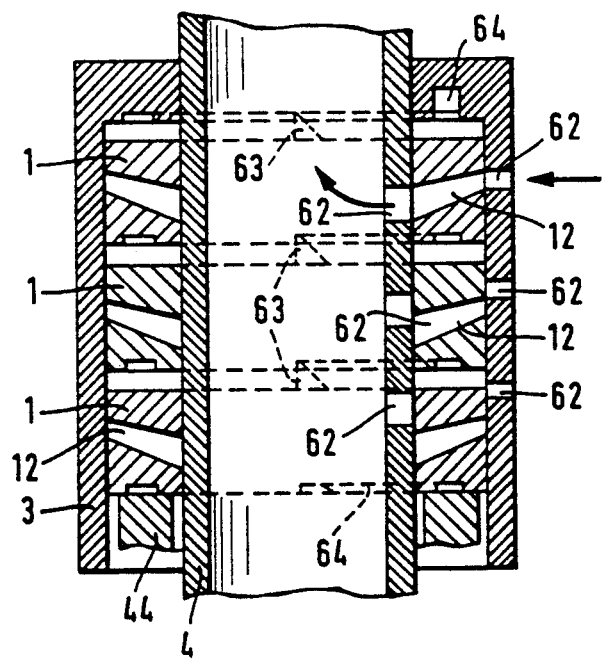
Fig. 14·C

POWDER INHALER

The present invention relates to a powder inhaler for administering multiple doses of medicaments in powder form from prefilled dosage chambers, for example in the treatment of asthma.

BACKGROUND OF THE INVENTION

Powder inhalers are being increasingly used nowadays as dosing and inhaling apparatus in the treatment of asthma by inhalation. This is because of objections, on ecological grounds, to conventional 2× metered dose aerosols because they have used halogenated hydrocarbons as the propellant gas.

A further disadvantage of 2× metered dose aerosols is that the patient must be able to coordinate the release of spray and inhalation. This is not always possible during an acute asthma attack in which the patient is under great stress. Powder inhalers eliminate the need to coordinate inhalation and spraying, since the air inhaled by the patient activates the dosage release.

In conventional powder inhalers (for example as disclosed in Published European Patent Application EP-A 406 893) each dose of the active substance is contained in a single hard gelatin capsule. The capsule is inserted in an apparatus where it is punctured by several pins. The contents of the capsule are released and carried along by the flow of air inhaled by the patient. They are then transported to the lungs of the patient.

This type of powder inhaler has the disadvantage that a diluent, such as lactose, has to be added to the active ingredient to fill the capsule and to ensure dosage accuracy. In some patients inhalation of the finely distributed lactose powder can lead to airway irritation.

Moreover there is no guarantee that the punctured capsule is completely emptied and that its content is available to the patient. What is more, there is a danger of fragments of capsule being inhaled as well.

German Patent DE-P 27 04 574 discloses an inhaler for a pharmaceutical enclosed in a capsule where the capsules are stored in a rotatable magazine that is moved forwards by rotating the outer casing of the inhaler.

Apparatus that dispenses with capsules may avoid the above disadvantages. Thus, for example, the Turbuhaler ® manufactured by Astra works without lactose as an auxiliary substance and the pharmaceutically active substance is inhaled directly. Each apparatus permits withdrawal of two hundred doses. The pharmaceutical is stored in a storage container in the form of spherical aggregates of a micronized powder. During inhaling, these aggregates disintegrate into the micronized powder which is respirable.

Administration of the powder is aided by a rotatable dosage disk. The spherical agglomerate of the pharmaceutical is pressed from above into a group of four measuring openings which determine the amount of the granulate to be released. The granulate is measured volumetrically.

The dosage disk is rotated further and, with the four dosage holes filled, reaches a part of the inspired air flow and the active substance is torn out of the dosage holes. The spherical aggregates are divided up in the spiral-shaped flow of the mouthpiece and inspired as micronized powder.

A disadvantage of the Turbuhaler ® is that the dosage holes can become blocked and the dosage accuracy can decrease progressively as the apparatus is used. Furthermore a not inconsiderable amount of the pharmaceutical accumulates in the mouthpiece with the number of dosages released. This constitutes a risk for the patient, since there is a danger that too much of the pharmaceutical will be inspired at once.

Published European Patent Application EP-A 407 028 describes a powder inhaler that scrapes a measured amount from a compact supply of pharmaceutical using a scraper and allows this amount to be transferred into a cyclone chamber by the airstream of the patient. The mixture layered in the cyclone is inspired by the patient.

Published European Patent Application EP-A 387 222 describes an electronically controlled device for the release of a pharmaceutical which responds to the noise created by the flow of the inspired air and releases a dose from the supply of medication.

Published European Patent Application EP-A 237 507 describes a powder inhaler with impact surfaces that divide up the supply of medicament released from the dosage container.

Published European Patent Application EP 69 715 describes a powder inhaler activated by the stream of air inspired by the patient. It is possible for the inspired air stream from a dosage device, which can be rotated into the inspired air stream, to draw a volumetrically measured amount of pharmaceutical with it.

SUMMARY OF THE INVENTION

It is an object of the invention to provide the patient with an inhalation device which provides accurate dosage of medication over a long period of time, which is easy to operate and simple to clean, which does not give rise to coordination problems between release of medication and inhalation, and which operates without a supply of energy.

A further object of the present invention is to provide an apparatus which makes the dose available immediately, eliminating the need to laboriously insert a hard gelatin capsule into the apparatus or to pierce a blister foil.

A still further object of the present invention is to provide an apparatus in which, once the prefilled dosage chambers are empty, a new cartridge with filled dosage chambers can be inserted. This permits the mechanical device of the powder inhaler to be used many times.

The particles of active substance which the asthma patient inhales in accordance with the present invention contain virtually no larger-sized constituents or agglomerates. 90–95% of the particles released are of respirable size. As a result, less active substance is deposited in the mouthpiece, mouth or throat.

A further advantage of the inhaler of the present invention is that the air stream carrying the particles is surrounded by a particle-free air stream. This reduces deposition of the pharmaceutical in the mouth and throat region of the patient. As a result, the incidence of local side effects in the mouth and throat region is reduced and the efficacy of the medication is increased.

A further advantage of the present invention is that the kinetic energy of the inhaled air stream of the patient that is generated by the inhaling patient serves as the energy source that releases the dose. This divides the active substance mixture up into respirable particles.

There is no need for an external energy source, for example a battery as disclosed in PCT applications WO 90/13328 or WO 90/13327.

The high dosage accuracy of the inhaler of the present invention, for all doses, is achieved by having an individual dosage chamber, filled with active substance mixture by the manufacturer, for each dosage of the pharmaceutical. This procedure rules out faulty fillings due to changes in the powder formulation in the storage container, such as can occur in apparatus which has a dosage disk.

Agglomeration of the reservoir of medication due to changes in air temperature and humidity is also prevented by the inhaler of the invention, since the dosage rings (1) are reliably closed off from the outside air by positioning in the ring canal (53) between the cylinders.

The invention will be better understood from the following detailed description of a preferred embodiment, reference being made to the drawings.

BRIEF DESCRIPTION OF FIGURES OF DRAWING

In the drawings,

FIG. 4 shows the guide grooves.

FIGS. 5A and 5B show the mechanism in the guide grooves.

FIG. 6 shows the inhaler in the filled condition.

FIG. 7 shows the inhaler in the empty condition.

FIG. 8 shows the mouthpiece.

FIGS. 14A-C show the construction according to Example 4.

Figure 15:
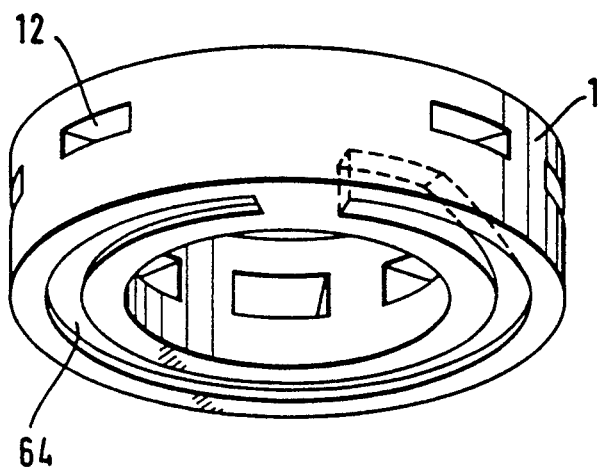
Figure 16:
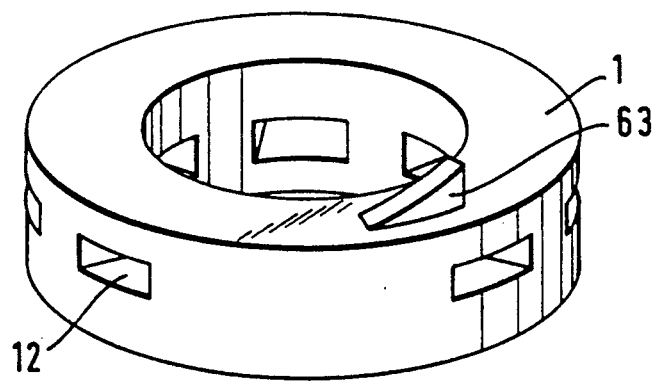

FIGS. 15 and 16 show the dosage disk of Example 4.

FIGS. 17 to 20 show the inhaler of Example 5.

Figure 21:
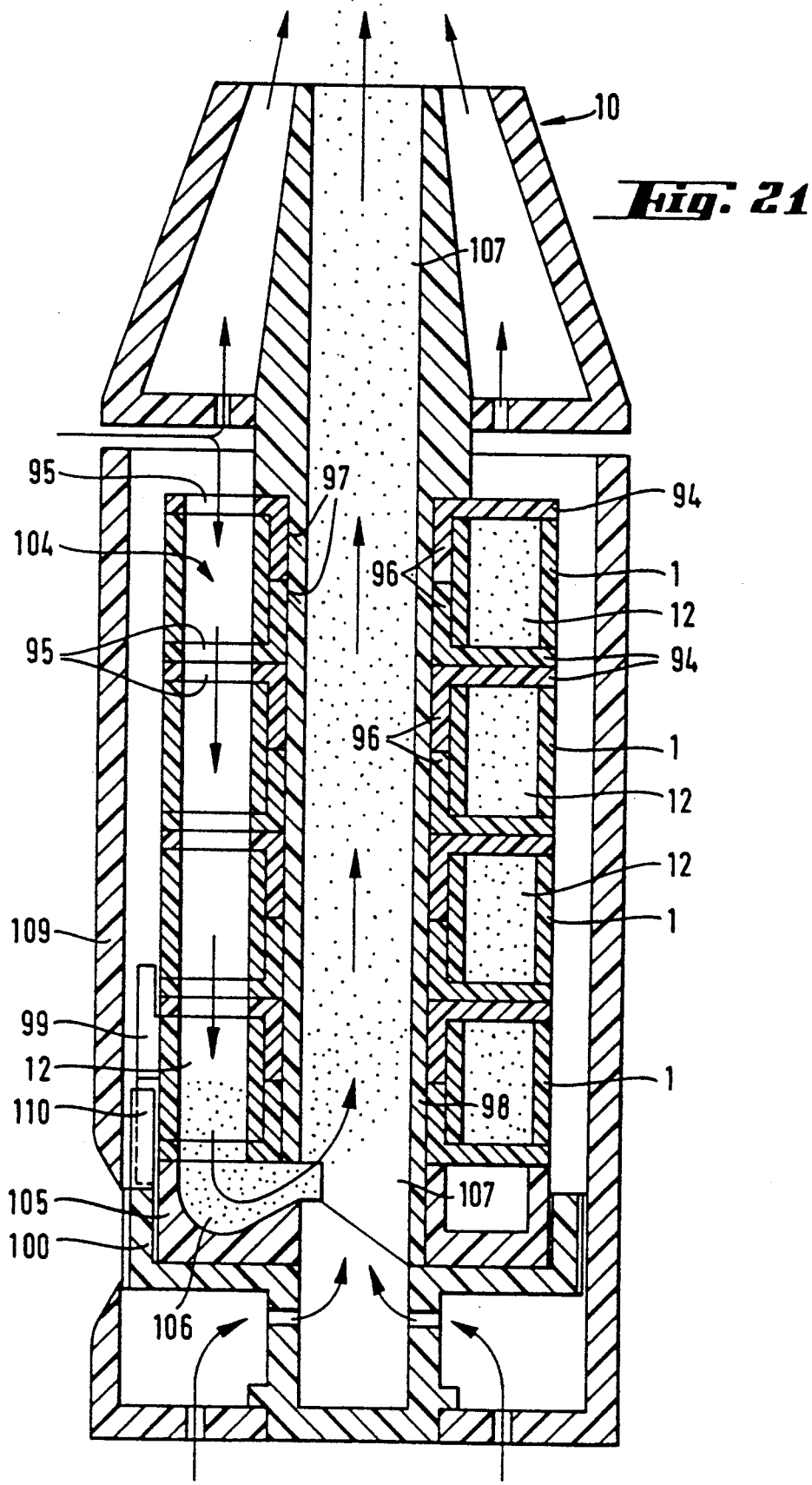

FIG. 21 shows the inhaler of Example 6.

Figure 22:
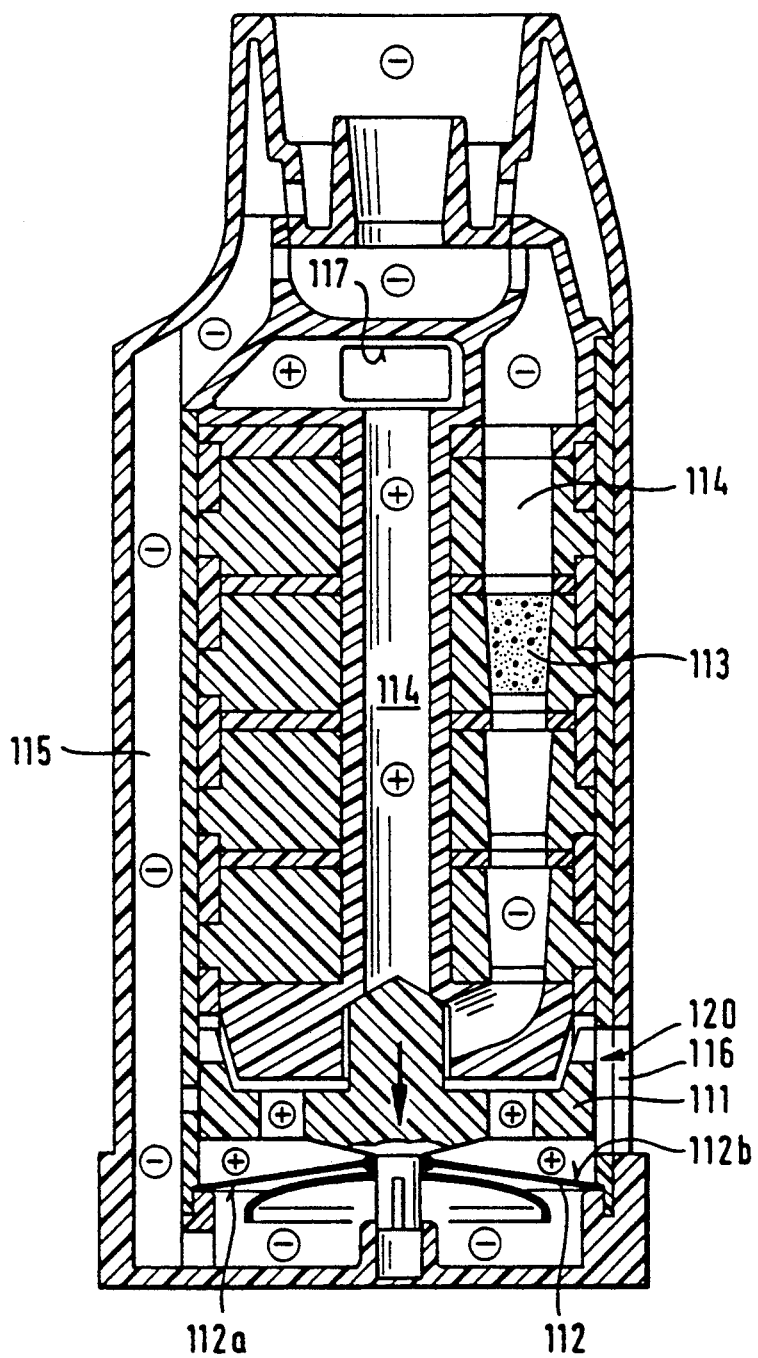

FIG. 22 shows a further embodiment of the invention.

Figure 23:
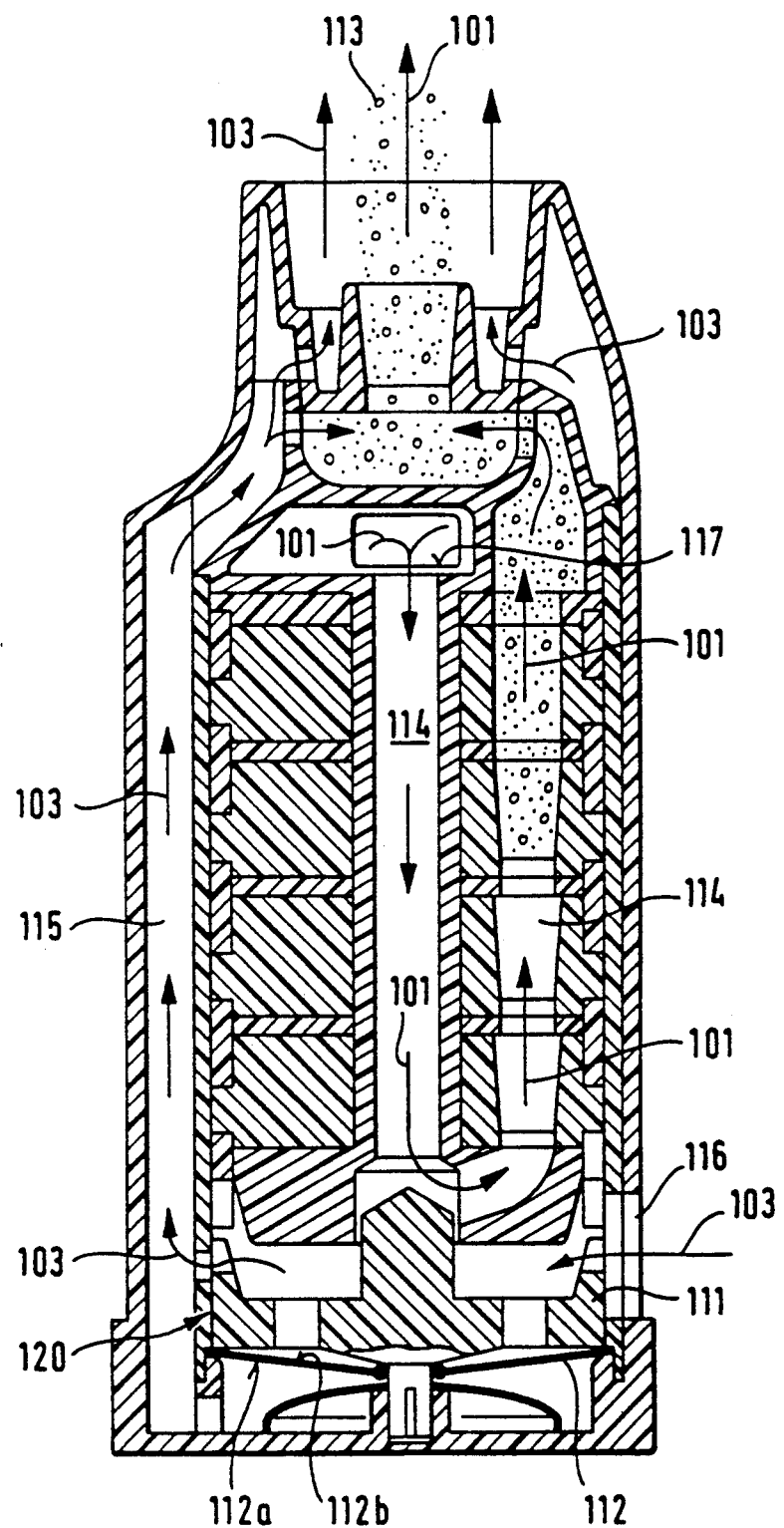

FIG. 23 shows another view of the inhaler of FIG. 22.

DETAILED DESCRIPTION OF PREFERRED EMBODIMENTS

Asthma patients always carry an inhaler with them, so as to be prepared to inhale medication immediately when they have respiratory difficulties. Therefore, the inhaler must be protected against mechanical shocks and against humidity in order to prevent the active substance being spun out of the dosage chambers (12). This is also achieved by enclosing the dosage rings (1) in the ring canal (53).

Figure 1:
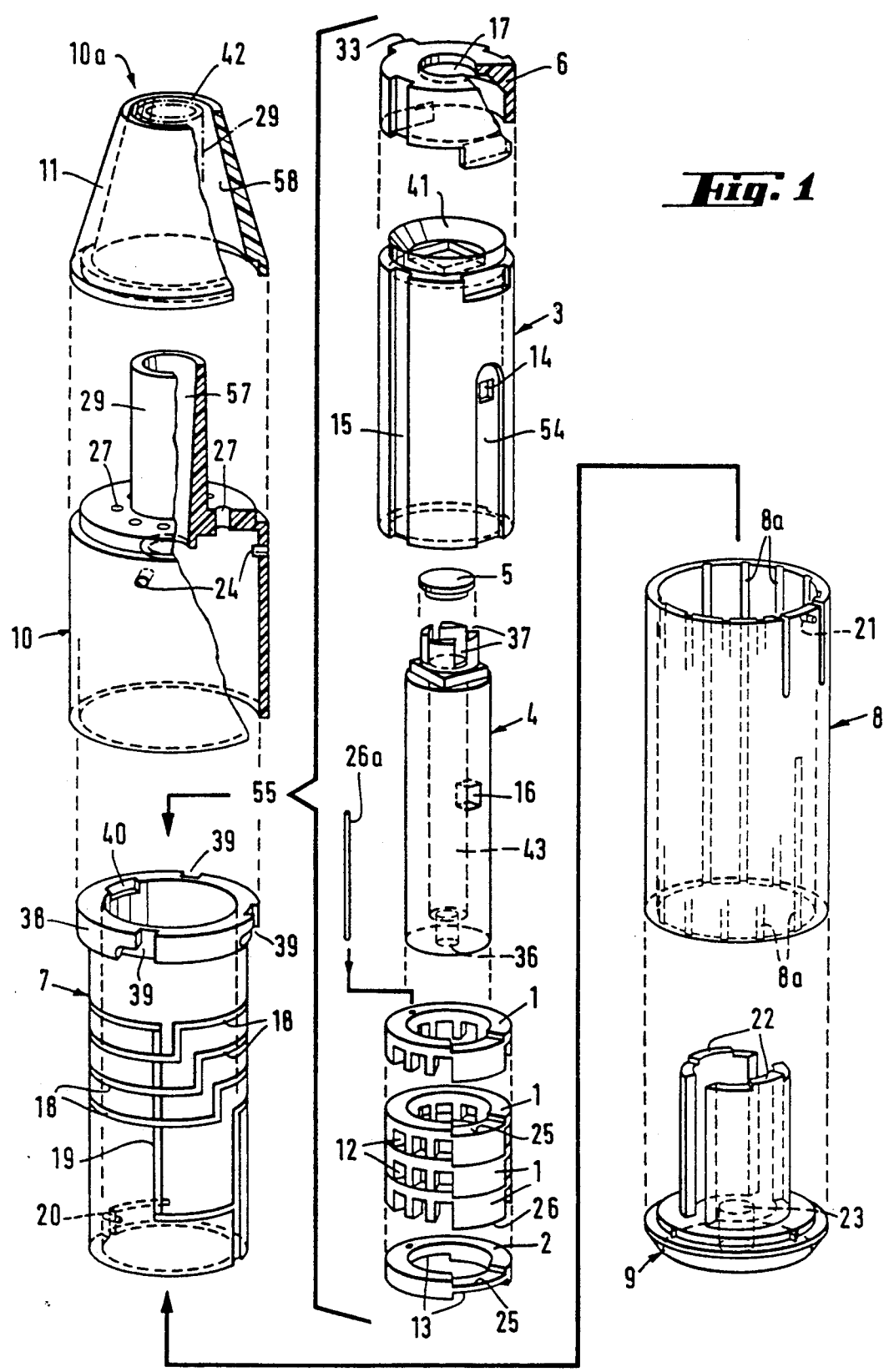
FIG. 1 shows an exploded drawing of the complete inhaler according to Example 1.
Figure 2:
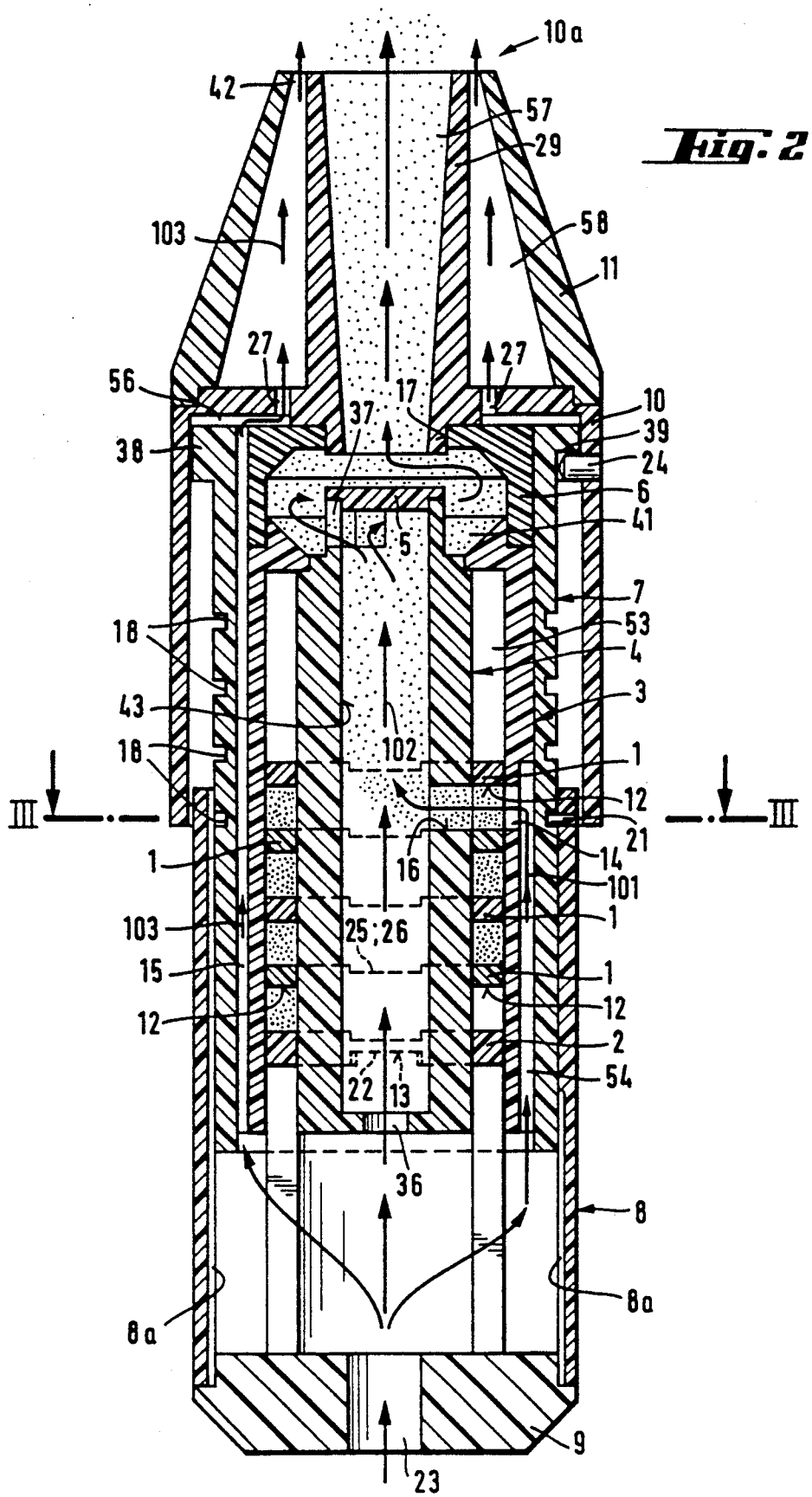
FIG. 2 shows a longitudinal section of the inhaler according to Example 1 with the air streams.
Figure 3:
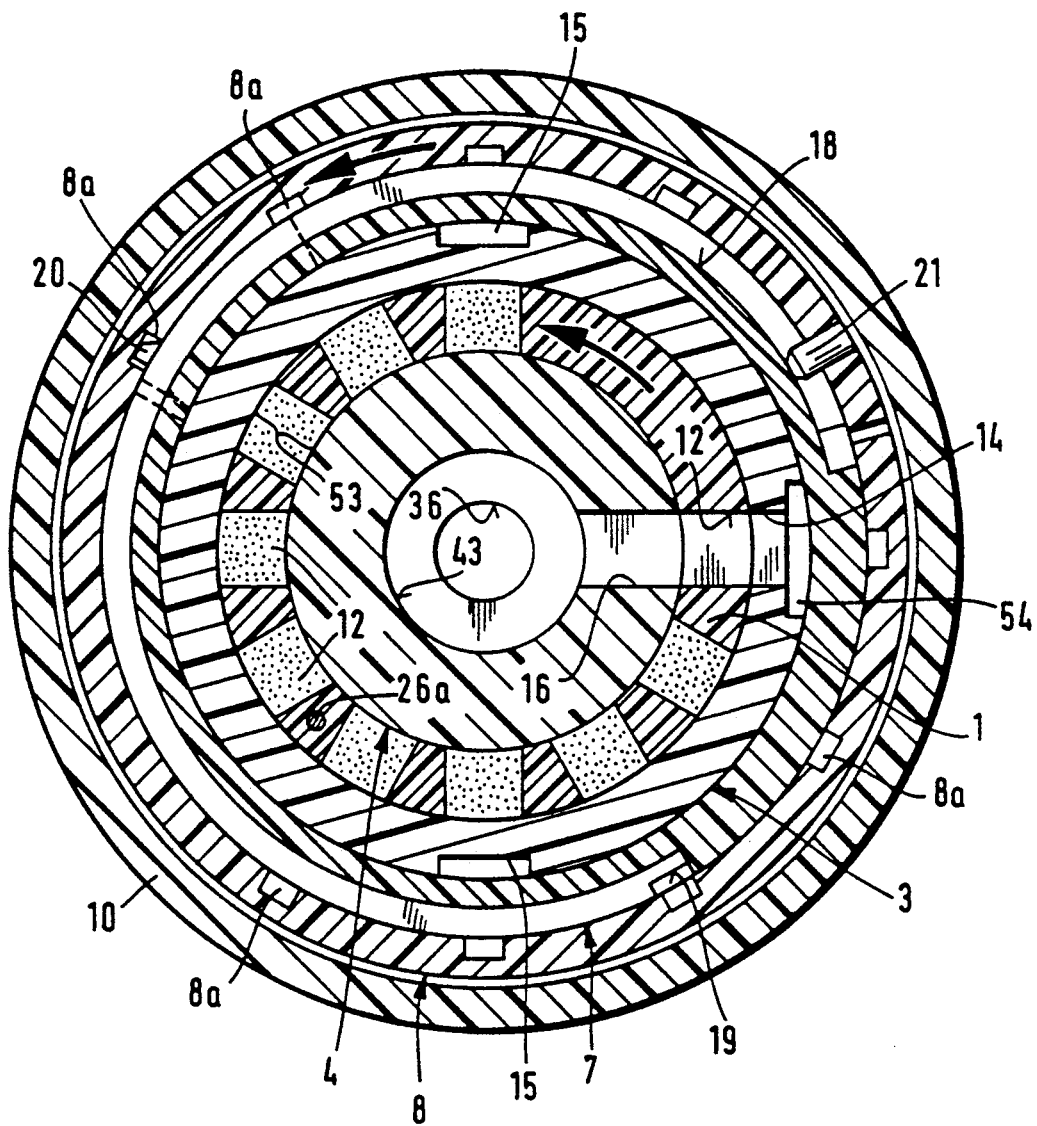
FIG. 3 shows a cross-section along the lines III—III of FIG. 2.

As shown in FIG. 1, the powder inhaler of the invention consists of four main parts: a disposable cylinder (55) composed of parts 1, 2, 3, 4, 5 and 6, a guide cylinder (7), an outer cylinder (8) which includes an inhaler base (9) and a mouthpiece (10, 11, 29). The powder inhaler can be dismantled into these parts for cleaning and refilling.

The disposable dosage cylinder (55) consists of an inner cylinder (4) with lid (5) with a central boring (36) on the base to admit part of the inhaled air and with an opening (16) on the side wall for the throughflow of another part of the air stream. A lid (5) is provided at the upper end of the central boring (43) which ensures that the inhaled air can only flow away in tangential direction through the tangential air ducting slits (37) into the cyclone chamber (41).

The inner cylinder (4) is enclosed by an outer cylinder (3) in such a way that it is impossible to rotate the two cylinders against each other. In the illustrated embodiment, this is achieved, by a close-fitting connection of the inner cylinder (4) with the outer cylinder (3) on the upper side of the cylinders. However, other means can achieve the same effect. The outer cylinder (3) has a lateral aperture (14) for inhaled air, aligned with the opening (16) of the inner cylinder (4).

When air is inhaled, the air stream containing the drug dose is immediately conducted from the central boring (43) of the inner cylinder (4) through tangentially disposed openings (37) into the cyclone chamber (41).

There, the centrifugal forces divide up any still remaining agglomerates into respirable particles by means of impact against each other and impact against the wall of the cyclone chamber and on the lid (5). Drag forces then conduct these particles to the canal (29) of the mouthpiece (10) via the opening (17) in the top of the disposable cylinder 55.

The four dosage rings (1) and the end disk (2), which constitute the active substance magazine, are disposed in the intermediate space (53) between outer cylinder (3) and inner cylinder (4).

EXAMPLE 1

The dosage rings (1) and the end disk (2) can either be composed of individual rings or be made in one piece. The rings engage with each other in such a manner that all four dosage rings (1) can be rotated simultaneously and evenly. The torsional closure of the individual dosage rings (1) as well as the end disk (2) can be effected by notches (25) and protuberances (26) that complement each other. An additional steel pin (26 a) can further increase stability. The individual dosage rings (1) as well as the end disk (2) can also be made from a single piece. (For production injection molding is always used). The four dosage rings (1) are provided with recesses so that, when the rings are stacked upon each other, dosage chambers (12) are created which can accommodate a specific amount of pharmaceutical powder or a mixture of active substances and auxiliary substances.

The disposable dosage cylinder (55), composed of the dosage rings (1), the end disk (2), inner cylinder (4) and outer cylinder (3) and cyclone chamber (6) is housed in the guide cylinder (7). On its upper side, the guide cylinder has a flange (38) with, for example, a system of notches (39) incorporated therein, which forms a bayonet closure with protuberances (24) extending inwardly from the mouthpiece (10). These permit the guide cylinder (7) to be en gaged with the mouthpiece (10). It is also possible to replace this arrangement with a snap closure.

A recess (40) is provided at the upper edge of the guide cylinder (7). This engages with a protuberance (33) on the cyclone chamber (6), so that the disposable dosage cylinder (55) can snap into the appropriate position. This snap action prevents faulty assembly by the patient.

The outside of the guide cylinder (7) has grooves (18, 19) for guiding the outer cylinder (8) and the inhaler base (9). These provide a means by which the end disk (2) of the dosage ring stack can be driven via the drive pieces (22). On the lower edge of the guide cylinder (7) there is a catch (20) which snaps into a groove (8a) of the outer cylinder (8) after each 30 degree rotation of the inhaler base.

Two semicylindrical drive pieces (22) are provided at the upper side of the inhaler base (9) which engage with the depressions (13) of the end disk (2) of the dosage ring stack.

The inhaler base (9) has a central boring (23) which serves as an inlet for air to be charged with active substance, for a false air stream and for the jacket stream. The air for the jacket stream can also be fed in by other means, for example from the side, through an opening in the mouthpiece. The mouthpiece (10) is secured by means of a bayonet closure to the flange (38) of the guide cylinder (7). The mouthpiece (10) consists of two easily detachable parts. It contains an outflow tube (29) which is conical on the inside surrounded by a casing (11). When the inhaler is assembled, there is an intermediate space (56) interposed between the cyclone chamber (6) and the mouthpiece (11). Air can flow through this intermediate space. The conical shape of the canal (57) in the mouthpiece (10) prevents a second cyclone effect. This ensures that far less of the pharmaceutical becomes deposited on the walls of the mouth piece than with a cyclone effect in the mouthpiece without outflow tube (29).

The inhaler base (9) is pushed in an axial direction until the catch (21) reaches the first ring (18) in the guide cylinder (7).

At the same time a form-fitting contact is created between the drive pieces (22) of the inhaler base (9) and the drive ring (2) of the dosage cylinder stack so that the drive ring (2) and the dosage cylinder (1) can be rotated by rotating the inhaler base (9).

A dosage chamber (12) filled with powder is rotated in front of the air intake hole (14) in the other dosage cylinder (3) and can now be emptied by means of an air stream (101) into the canal (43) via the opening (16) provided in alignment with the inner dosage cylinder (4). The false air stream (102) conducted through the air inlet opening (36) then conveys the powder further.

From this stage in the rotation, the catch (20) only permits further rotation to the right.

After inhaling the first dose from a dosage chamber (12) the patient can rotate the second and following doses into position in front of the outflow hole (16) of the inner dosage cylinder (4).

After inhaling the last dose of the first ring (1) in the active substance magazine the patient continues to rotate until the blockage of the catch (21) by the end of the first control curve (18) prevents further rotation and hence a renewed positioning in front in front of the outflow hole (16) of an already emptied dosage chamber (12).

The catch (21) engages in the control curves (18) on the guide cylinder (7) in such a manner that the outer cylinder (8) and the base piece (9) secured by means of a clamp seat with the guide pieces (22) engaged in the depression (13) of the end disk (2) of the dosage disk (1). This guides a dosage chamber (12) of the corresponding dosage disks (1) filled with active substance or with a mixture of active substance and auxiliary substance in front of the air hole (16).

The inhaler base (9) with outer cylinder (8) can now only be displaced in axial direction [axial area of the channel (18)] until the catch (21) reaches the guide channel (18) for the rotation of the second dosage disk (1). The remaining dosages in that disk can be withdrawn from the dosage chambers (12) by means of rotation to the right.

In the embodiment shown in greater detail in the drawings, four dosage disks (1) are for example disposed one above the other.

The third and the fourth dosage disks are then emptied in sequence.

After the last dosage chamber (12) has been emptied, this being the fortieth in the example, the lower part of the inhaler (8,9) can neither be rotated further nor transported further in an axial direction. Further rotation to the right is prevented by the upper catch (21) and by the control curve (18) (at the end of the channel).

Rotating back of the lower part of the inhaler (8,9) is prevented by the catch (20) in the lower part of the guide cylinder (7), which is snapped into a corresponding chamfer (8a) of the outer chamfered cylinder (8). Axial withdrawal of the lower part of the inhaler (8,9) along the channel (19) is prevented by the shallower depth thereof as compared to the channel (18) in such a way that the displacement of the cam follower (21) by the inner jacket surface of the mouthpiece (10) needed for the transition of the cam follower (21) from the deeper channel (18) into the shallower channel (19) is prevented. It is only possible to guide the cam follower (21) into the channel (19), or to remove the lower part of the inhaler (8,9) axially, after removal of the mouthpiece (10) (bayonet 24/39). A new disposable cylinder (55) can then be inserted after the mouthpiece (10) has been cleaned and dried.

The inhaler can then be reassembled and rotated into the position to permits inhalation of the first of a new series of doses.

In another preferred embodiment of the dosage disk drive, the dosage disks are not moved jointly by one mechanism, but drive each other in succession by means of carrier devices.

In this embodiment, the disposable dosage cylinder consists, as described above, of an inner and an outer cylinder. The annular intermediate space between the cylinders accommodates the dosage disks.

Each dosage disk can occupy a "dead" or inactivated position. The width of the inactivated position is such that outflow openings (14,16), which are no longer needed, are reliably sealed. With, for example, seven dosages per dosage disk, the part of the angle of rotation available for sealing purposes is 45°. The drive ring (44) for the rotary movement of the dosage disks is disposed at the lower end of the dosage stack. The blow-out opening in the inner cylinder leads directly into the dismantling device (41) (cyclone chamber or impact plate).

EXAMPLE 2

In an example of an embodiment of the invention, the dosage disk has two wedge-shaped elevations (45) on its upper surface which are disposed along arcs of a circle of differing radii.

When the dosage disks (1) are rotated, only the tip of the wedge-shaped elevation (45) is in contact with the underside of the next dosage disk (1) so that only minimum frictional force is transferred. This frictional force is negligibly small as compared to the frictional forces which are exerted from the wall of the outer cylinder onto the dosage disk (1). For this reason the following dosage disk (1) is only moved when the wedge-shaped elevations (45) of the first dosage disk (1) engage in the matching wedge-shaped depressions (46) of the second dosage disk (1). Since the dosage disks engage with one another, the distance between them decreases. This reduction in length and meshing together is supported by a spiral spring (61) which presses the dosage disks (1) together. Each dosage disk can for example be rotated by 315° in order to empty seven prefilled chambers (12).

The air throughflow openings (62) are advantageously shaped as individual openings and not as a slit so as not to weaken the structure of the cylinders unnecessarily. A rigid housing is needed to provide the pharmaceutical powder in the dosage chambers (12) with reliable protection against moisture.

Since the dosage disks (1) have to be emptied in succession, it is necessary to block the air stream off from disks not in use. This is achieved by the dead position of the non-rotatable dosage disks (1). The dead position of the prefilled dosage disks (1) is reached by not disposing any dosage chambers (12) over a specific extent of the dosage disks (1) so that the active substance of the dosage chambers lies closely against the inner wall of the cylinder, thereby blocking off the stream of air. This no longer applies, however, to the emptied dosage disks (1) that rotate as well, since the already emptied dosage chambers (12) are sequentially guided in front of the blow-out openings (62).

This is a disadvantage since the air stream which blows through the pre-filled chambers no longer suffices to transport the medicament out of the chamber. Under these circumstances, reproducibility of the dose is no longer guaranteed.

Figure 9:
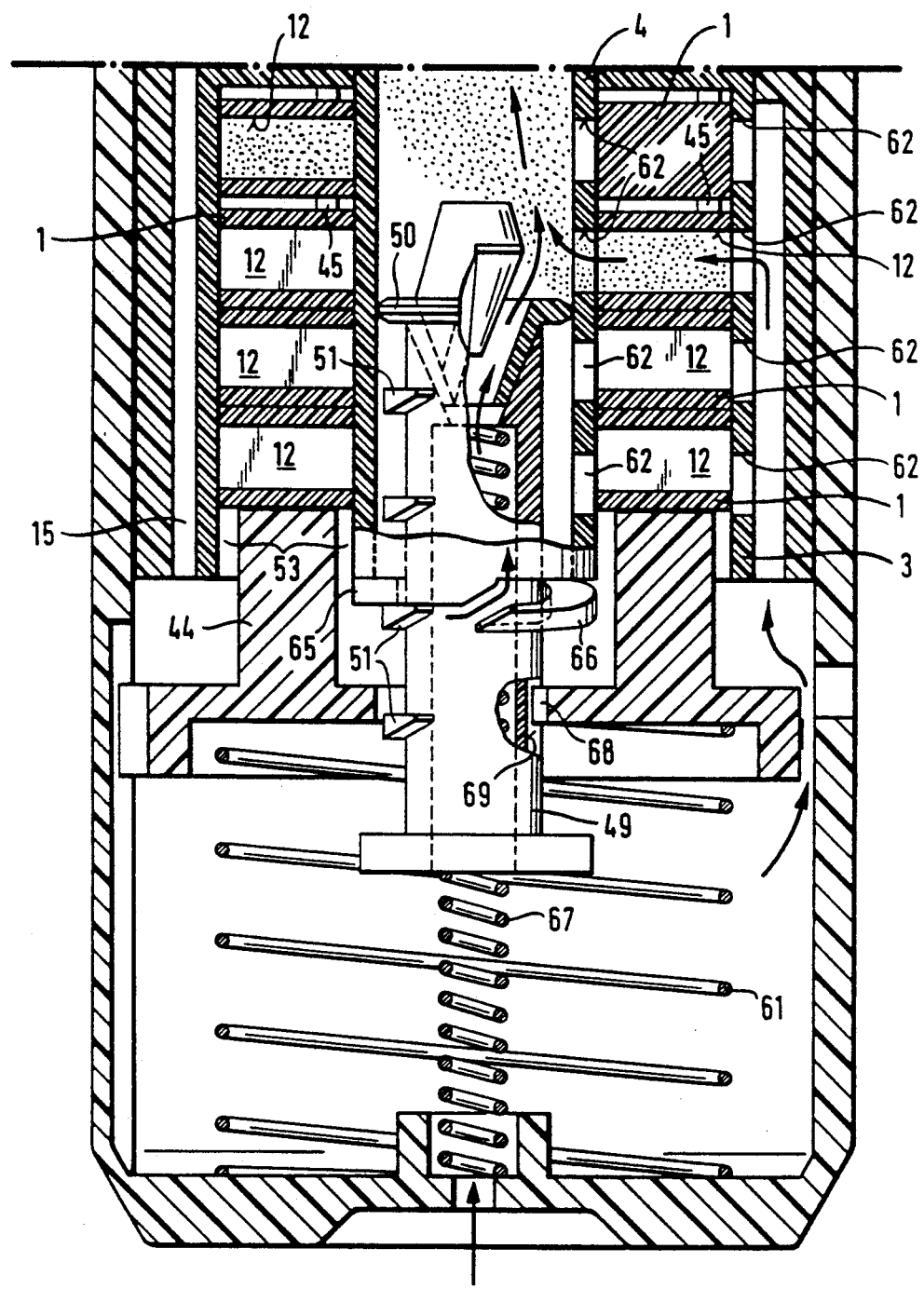
FIG. 9 shows a longitudinal section through the inhaler with the sealing piston.
Figure 10:
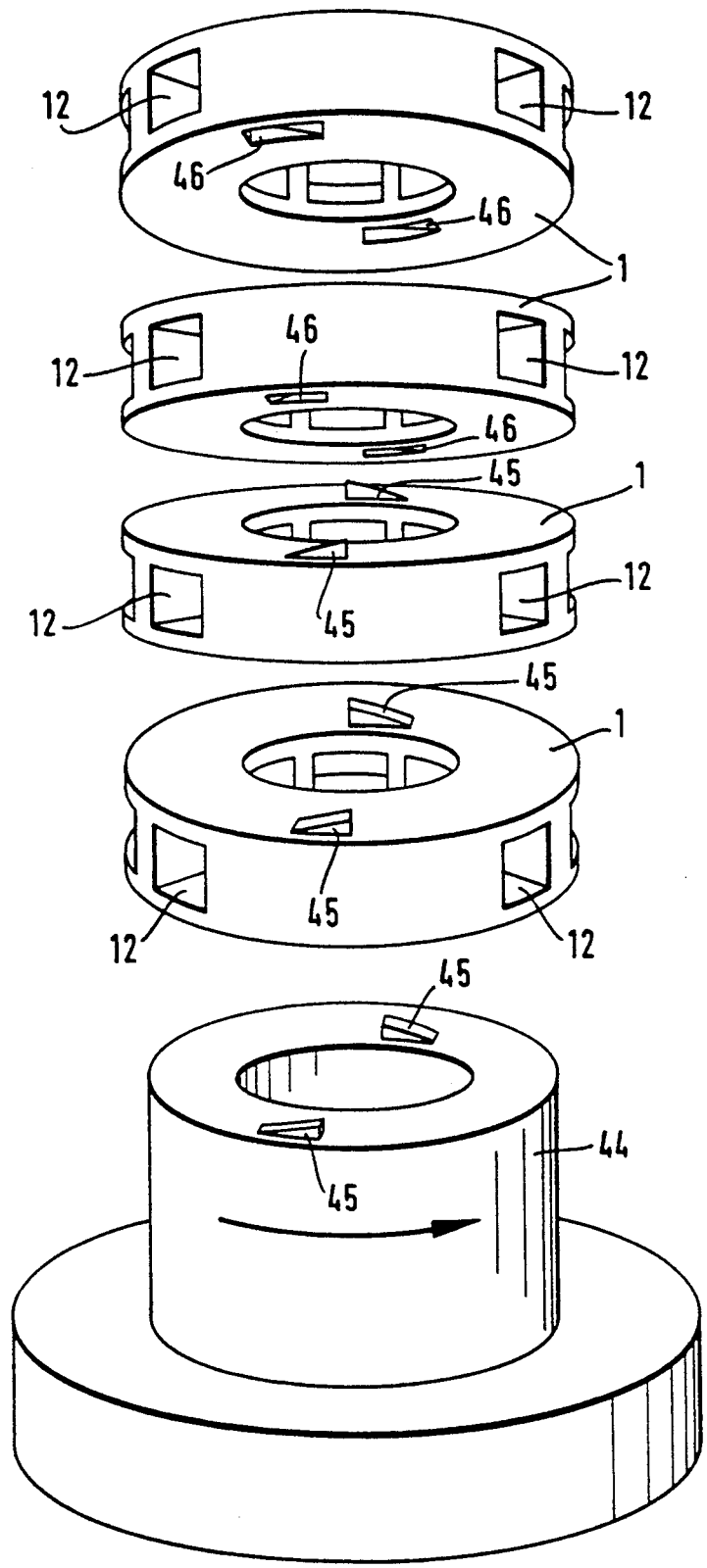
FIG. 10 shows the mechanism of the mutually actuating dosage disks.
Figure 11:
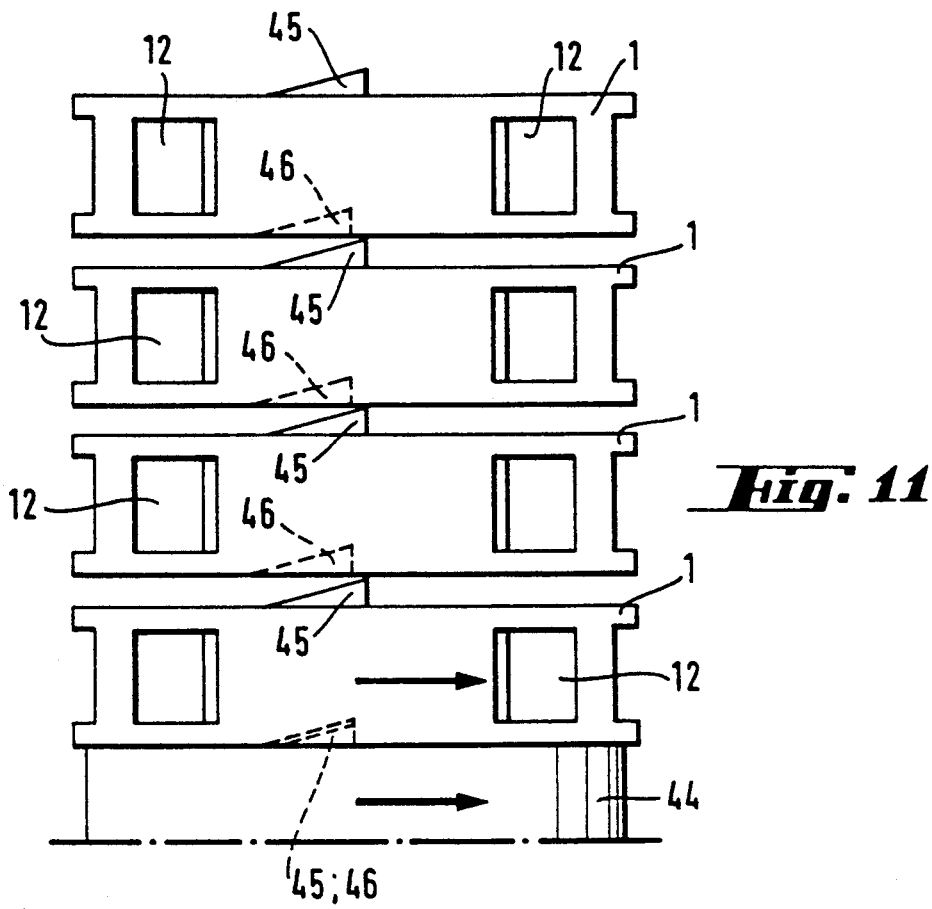
FIGS. 11 and 12 show details of the mutually actuating dosage disks.
Figure 12:
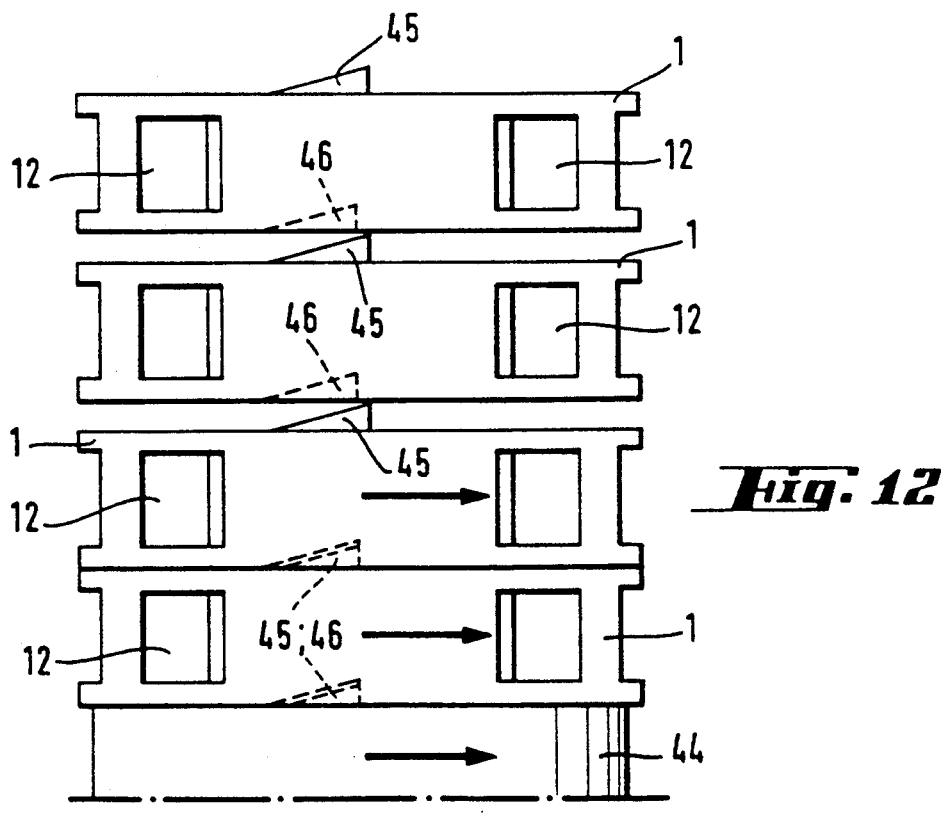
Figure 13:
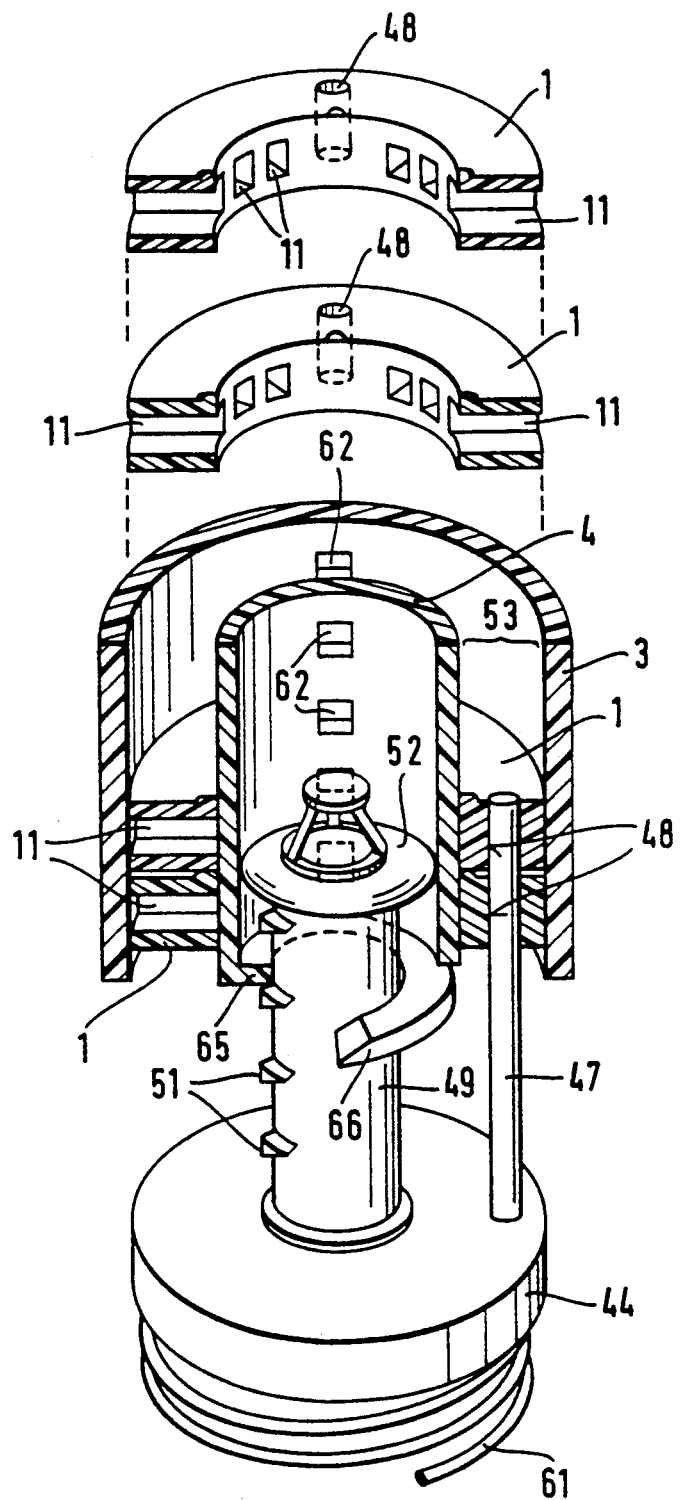
FIG. 13 is an exploded drawing of the inhaler of Example 3.

The following steps are, for example, taken to suppress the undesired air stream through the emptied dosage chambers:

An axially displaceable cylindrical piston (49) is provided (see FIGS. 9 and 13.) that has a spring (67) admitted therethrough and with a sealing element (50) provided at its upper end. This piston is moved upwards synchronously with the dosage disks (1) and blocks the dosage disks (1) lying under the sealing element (50) from the stream of air. The depth of immersion of the piston into the inner cavity of the cylinder is determined by a plurality of wedge-shaped protuberances (51) at the outer piston wall and by guide devices (65,66) on the base of the inner cylinder.

The guide device (65,66) consists of a flange with the same outer diameter as the cavity of the inner cylinder and with a smaller internal diameter. It prevents the wedge-shaped protuberances (51) from sliding past the outer piston wall. The flange (65) is only secured over half the circumference to the inner cylinder, the remaining circumference being covered by the freely suspended flange (66).

The freely moveable part (66) of the flange (65) has a bevelled end. When the drive ring (44) and the piston (49) are rotated [associated together so that they cannot turn but are axially slidable by means of the protuberance (68) and the spring (67)], the first wedge-shaped protuberance (51) rotates along the firm part of the flange (65) and, after the chambers in the first dosage ring have emptied, reaches the slit which is formed by the suspended part of the flange (66).

The wedge-shaped protuberance (51) slides through the slit and permits displacement of the piston (49) through spring resistance by the height of one dosage disk (1). The emptied dosage disk is thus segregated from the air stream and is out of the way.

EXAMPLE 3

Instead of the wedge-shaped protuberances (45) and slits (46) for transporting the dosage disks (1) it is also possible to provide an eccentrically disposed pin (47) fitted to the drive disk (44). The pin (47) dips into borings (48) of, in each case, the next dosage disk (1), the depth of penetration being controlled by an arrangement (51), (65), (66). This associates the piston firmly with the drive disk.

In another embodiment (not shown) the elements 51, 65, 66 can be dispensed with. In the initial position, the first dosage disk is in a dead position and the pin (47) engages in a boring (48) of the first dosage disk (1). Further penetration of the pin (47) is prevented by the pin (47) engaging against the second dosage disk. The full dosage disks are rotated slightly away from each other so that the borings (48) are no longer precisely aligned.

After successive rotation of the chambers has emptied the first dosage disk, the pin falls into the now exposed boring (48) of the second dosage disk (1) and constitutes a rotatable connection. The seal ring (52) applied to the upper side of the piston (49) blocks the air stream off from the already emptied dosage rings (1).

EXAMPLE 4 FOR A DRIVE MECHANISM

Instead of using a piston (49) of differing depth of penetration as a means of blocking off already emptied dosage chambers (1), it is also possible to use a construction in which the air throughflow holes of the outer wall of the disposable dosage cylinder are not as high as the air throughflow holes of the inner wall of the disposable dosage cylinder. The passage surface of the dosage chambers therefore increases from the outside inwards. In the initial arrangement, the dosage disks (1) lie packed closely together. The protuberances (63) on the upper side of each dosage disk (1) engage in a depressed area of the groove (64) on the underside of the superimposed dosage disk, the air throughflow slits in the outer wall of the cylinder are not disposed in alignment with the dosage chambers and the dosage chambers (12) are consequently blocked. By rotating the drive disk, the protuberance (63) on the upper side of the dosage disk emerges from one depression in the groove (64) on the underside of the superimposed dosage disk (1) and is axially displaced thereby so that the air throughflow openings are aligned.

After the chambers (12) of one dosage disk (1) have been emptied, the protuberance (63) is blocked in the groove (64) and thereby rotates the second dosage disk (1) that is moved downwards in front of the air inlet openings in the same manner as the first dosage disk (1).

EXAMPLE 5

Figure 17:
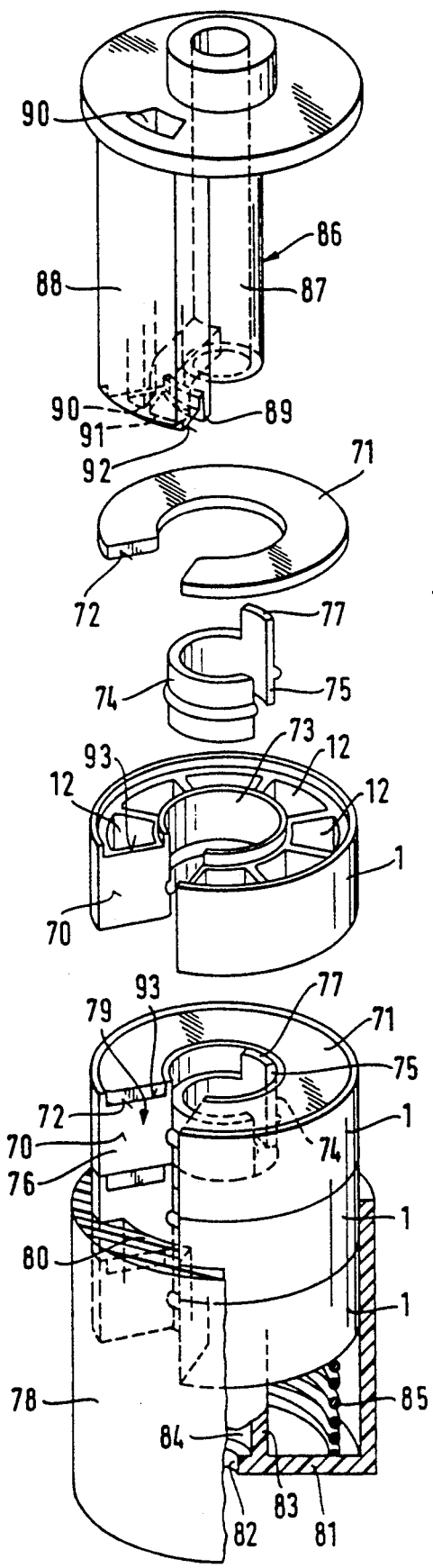
Figure 18:
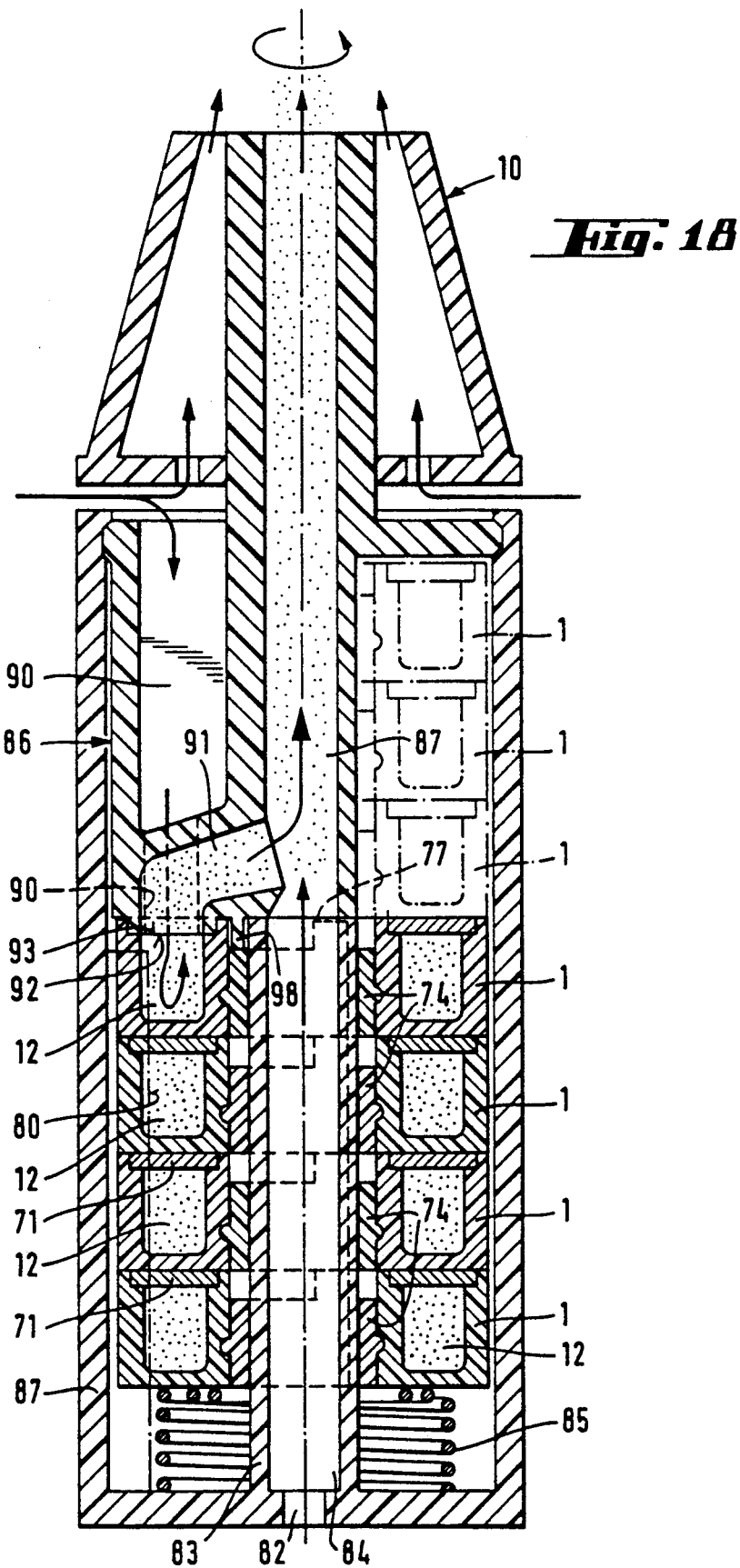
Figure 19:
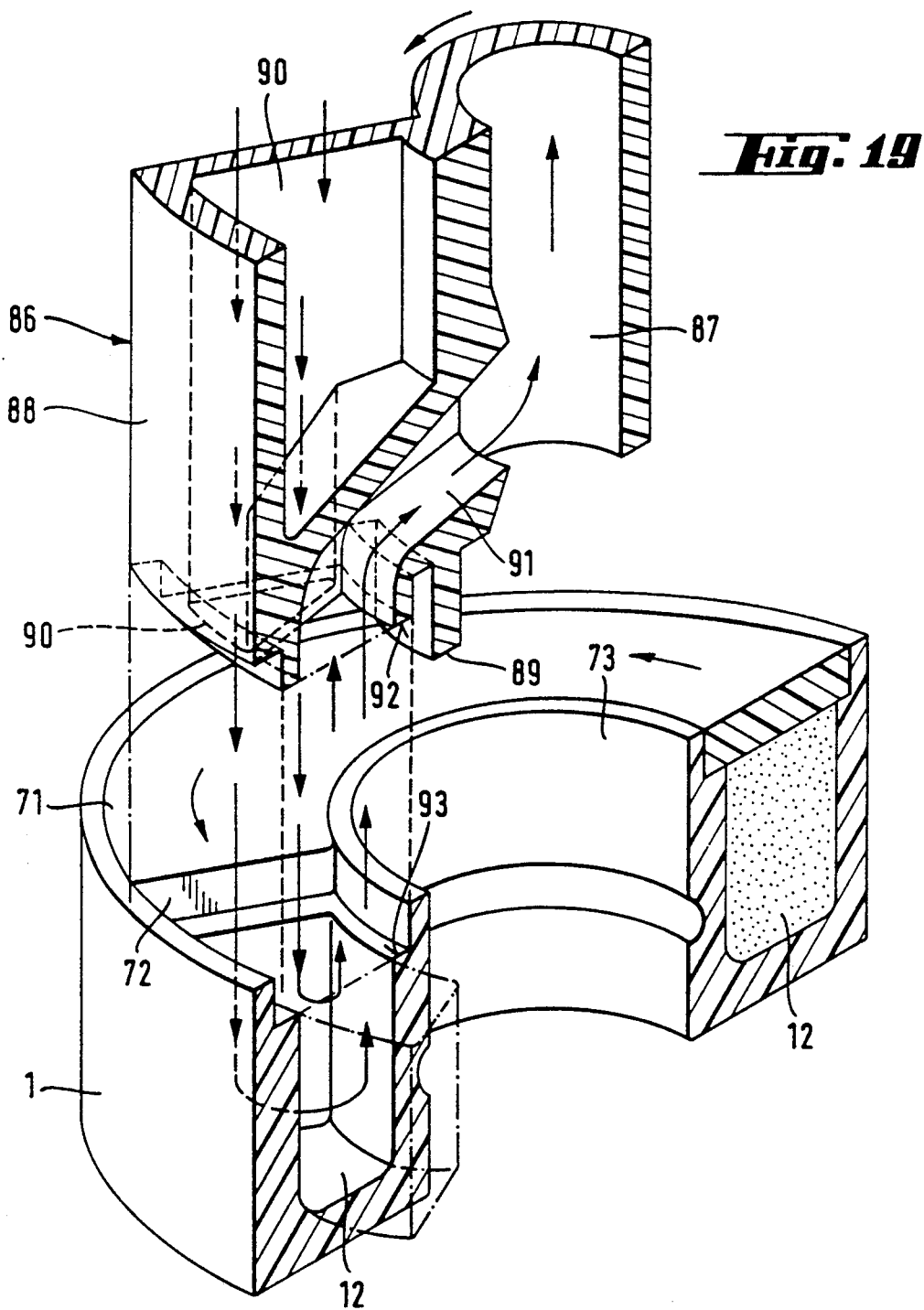

In FIGS. 17, 18 and 19 the principle of superimposed dosage disks (1) is retained, although the transport of air is substantially axial rather than not radial but axial. For this purpose, the dosage disks (1) have the form of a circular ring with dosage chambers (12) or troughs which are axially inserted in equal sectors in the surface of the circular ring in the direction of the circumference. A separation segment is withdrawn from the circular ring, forming a sectoral cutout (70) to form an "open" circular ring.

The axially formed openings of the chambers (12) are covered or closed by a lid (71) inserted flush in the circular ring which has a cutout (72) corresponding with the sectoral cutout of the dosage disk. The lid (71) is rotatably moveable and can be axially secured by appropriate means.

A locking element 74 (that does not move axially, but which is rotatable) is inserted in the central boring (73) of the dosage disk (1). The shape of the locking element (74) is basically tubular, and the sectoral cutout (75) is analogous to the cutout (70) of the dosage disk (1).

The area of the sectoral cutout (70,75) of the dosage disk (1) and of the locking element (74) can be made to overlap by rotatably displacing them towards each other so that a through sectoral canal (76) is formed. A stop nose or carrier nose (77) is provided to introduce a rotating movement component into the locking element (74) adjacent to the sectoral cutout (75) thereof.

In the initial state, that is when the full dosage disks (1) are inserted in the inhaler housing (78), the locking element first assumes a locking position where the sectoral cutouts (70,75) of dosage disk (1) and locking element (74) are not aligned.

The filled dosage disks (1) previously assembled in this manner are collected into a packet with all sectoral cutouts (70) of the dosage disks (1) forming an axial longitudinal canal (79), the dosage chamber openings being directed upwards.

A dosage disk packet formed in this manner is then inserted into the inhaler housing (78). A longitudinal rib (80) formed at the inner wall of the housing is fixed in the housing (78) so that it cannot rotate but is rendered longitudinally displaceable by means of sectoral cutouts (70) of the dosage disks (1) and lids (71).

A tube support (83) with an air inlet opening (82) is shaped centrally in the base of the housing (81) which passes through the dosage disks (1) and/or ring elements (74) axially and forms a gas canal (84).

The dosage disk packet is supported axially or pretensioned by a pressure spring (85) on the base of the housing.

A mouthpiece part (86) is inserted into the housing (78) from above, against the force of the spring, and held so that it can rotate. The mouthpiece part (86) has a tube support (87) continuing the central gas canal (84) of the housing (78) upwards, which carries a continuation (88) adapted in radially projecting manner to the sectoral cutouts (70,75) of the dosage disks (1) and ring elements (74) which stands aligned with it in the starting position of the inhaler.

Because of the blocking position of the locking element (74) the dosage disk package can only proceed under the action of the spring (85) until that upper side area of the locking element, which (lies) in the sectoral cutout area (70) of the dosage disk, runs onto a stop and control extension (89). The stop and control extension (89) projects underneath the mouthpiece part (86) in axial projections of the latter's radial extension (88) and also of the locking element (74).

The extension (88) of the mouthpiece part (86), which substantially has two canals (90,91), now lies with its outlet level (92) at about the same height of the outlet level (93) of the dosage chambers (12) of a dosage disk (1) in such a way that the end section of the extension on the outlet side engages in form fitting manner in the sectoral cutout (72) of the lid (71).

The axial length of the rib (80) in the housing (78) is so dimensioned that the torsion securing device of the upper dosage disk (1) only acts on the dosage disk itself, but no longer on the lid thereof.

By rotating the mouthpiece part (86) opposite the housing (78), it is possible to line up the extension (88) of the mouthpiece part (86), or the end section on the mouthpiece side thereof together with the sectoral recess (72) in the lid (71), with the corresponding dosage chambers (12).

Two canals (90,91) open into the outlet level (92) of the mouthpiece part (86), namely an air inlet canal (90), which introduces an air stream into the dosage chamber (12) and whirls up the pharmaceutical, and a discharge canal (91) which leads the whirled up pharmaceutical into the central canal (87) of the mouthpiece part (86).

At the latest when the mouthpiece part (86) is rotated after the last dosage chamber (12) has been emptied, the control extension (89) impinges on the carrier nose (77) of the locking part (74). This carries this element along in rotation and brings the sectoral cutout (75) thereof into alignment with that (70) of the dosage disk (1).

The sectoral canal (76) of the first dosage disk (1) (empty disk) is now open. The extension (88) is now aligned with the sectoral canal (76).

The dosage disk packet is now able to travel upwards under the effect of the spring (85) until the stop and control extension (89) of the mouthpiece part (86) impinges on the locking element (74) of the subsequent dosage disk (1), when the above described emptying process can be continued in analogous manner. The empty dosage disks (1) are stored above the outlet level (92).

Suitable blocking devices between the mouthpiece (86) and the housing (78) as well as visual operating state indicators are essential here and are not shown for sake of clarity.

Figure 20:
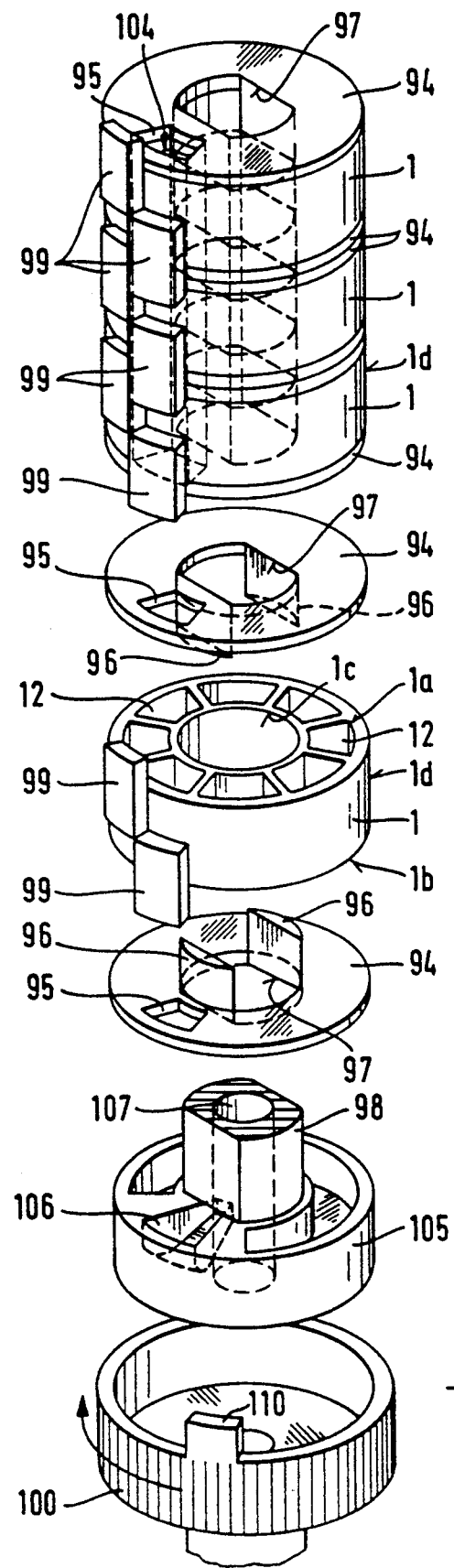

FIGS. 20 and 21 show a variant of the embodiment of FIGS. 17 to 19.

The dosage disks (1) used in this variant are also shaped in circular ring form with axial orifices evenly disposed in the direction of the perimeter. These orifices are closed at both their end faces (1a, 1b) by cover plates (94), thereby forming the dosage chambers (12).

The cover plates (94) are in each case provided with one orifice (95) corresponding to one dosage chamber (12).

The cover plates are provided with protuberances (96) engaging with the central boring (1c) of the dosage disk (1), creating a rotatable connection.

The central recess (97) of the cover plates (94) is shaped in such a manner that a torque can be induced into the cover plate (94) by means of an adapted tube support (98) passing through the central recess (97). Stops (99) are provided at the outer jacket surface (1d) of the dosage disks (1) by means of which the dosage disks (1) can be driven by one drive part (100) or by each other.

The dosage disks (1) filled with the pharmaceutical are superimposed in such a manner that one dosage chamber (1) is always empty, namely that which is aligned with the orifices (905) of the upper and lower cover plate (94). This forms an open canal (104) in the dosage disk (1).

A plurality of dosage disks (1) superimposed in this manner are now assembled into a packet in such a manner that all the open canals (104) are aligned and that the stops are adjacent to one another. The stack of dosage disks rests on a discharge chamber part (105) of the same outer diameter as the dosage disks (1) and a central tube support (98), the cross-section profile of which corresponds to the central recesses (97) of the cover plates (94). The discharge chamber (106) is aligned with the open canal (104) of the dosage disks (1). The trough-shaped discharge chamber (106) is associated with the central canal (107) of the discharge chamber part (105) or with the mouthpiece (10).

Rotary positioning of the cover plates (94) or of the openings (95) thereof to the discharge chamber (106) always ensures that one canal (104) above the discharge chamber (106), which serves as gas inlet canal, is always open.

A dosage disk drive ring (100) is placed in the inhaler housing (109) in such a manner that it can be actuated from outside and can catch into the stop (99) of the lowest dosage disk (1) with one protuberance (110). The lowest dosage disk (1) can only be rotated stepwise, bringing the corresponding dosage chambers (12) into alignment with the open canal (104) and emptying them.

After the last dosage chamber of the first dosage disk has been emptied, the stop thereof (99) impinges against the stop (99) of the next dosage disk (1) and takes this along in rotation. The next dosage disk can now be emptied in analogous manner.

EXAMPLE 6

This example describes an inhaler which has a device for adjusting the air stream. As a result of this device, the stream of air inhaled by the patient builds up a partial vacuum in the inhaler. Atmospheric pressure is present on the other side of the valve body (111) which means that there is an overpressure in relation to the stream of air inhaled by the patient.

The valve body (111) is maintained in the upper position by means of an elastic membrane (112) the coefficient of elasticity of which is such that the membrane (112) only deflects as from a specific force acting on the surface of the membrane (112).

The deflecting membrane (112) only pulls the valve body (111) downwards and releases the air streams (stream of inhaled air, false air stream and air charged with active substance) after a specific pressure difference between the inspiratory air side and the atmospheric pressure is exceeded.

This regulating mechanism can be incorporated in all the previously described embodiments of the powder inhaler.

The transport of air in Example 1 takes place as follows:

In this example of the invention, the air feed hole (23) in the inhaler base (9) is 7 mm in diameter. The air stream is divided into three partial air streams:

1) through the central boring (43) of the inner dosage cylinder (4), (false air 102), 2) through the longitudinal channel (54) of the outer dosage cylinder (3), by the air feed hole (14) in front of a prefilled dosage chamber (12) of the dosage disks (1), and through the prefilled dosage chamber (12), through the air feed hole (16) into the central boring (43) of the inner dosage cylinder (4), there the air stream (101) now charged with active substance particles combines with the false air stream (102) in order to flow upwards through the central boring (43) of the inner dosage cylinder (4) and through the tangential air ducting slits (37) into the discharge chamber or cyclone chamber (41) composed of cyclone (6), lid (5) of the inner dosage cylinder (4) and outer dosage cylinder (3). In place of the central boring (43) of the inner cylinder (4), in which the air laden with active substances or with a mixture of active substances and auxiliary substances enters the central boring (43), a constriction of the central boring (43) can be provided which accelerates the air stream as in the case of a Venturi nozzle and leads to a pressure drop. This pressure drop in the narrowest cross-section of the Venturi nozzle leads to an acceleration in the air stream laden with active substances and contributes to the active substance being blown out of the dosage chamber (12). At this point in the transport of air any remaining large aggregates of active substance particles or aggregates of auxiliary substance and active substance particles are divided up into respirable particles.

3) through the longitudinal channel (15), the intermediate space 56 and through the borings (27) of the mouthpiece (10) into the exit opening (42) between inner and outer mouthpiece to form the jacket stream (103). The jacket stream surrounds the particle-carrying air stream and keeps it away from the mouth and throat region.

The powder inhaler can be made of a medically acceptable plastics material. It may be appropriate to provide a drying agent in the powder inhaler.

The total pressure drop in the example of the embodiment of the inhaler is between 50 and 150 mbar with a respiratory air stream of 60 liters/minute.

The pressure drop through the unfilled inhaler at a respiratory air stream of 60 liters/minute is for example 30 mbar, 60 mbar when the central bypass is closed and 53 mbar without the jacket stream.

What is claimed is:

1. In a powder inhaler comprising a housing, having a mouthpiece opening for flow of air laden with active substance and an active substance magazine including means for incorporating the active substance or a mixture of active substance and inert components into an air stream guided through the inhaler, the housing comprising parts designed to be moveable against each other, and one housing part having an inlet opening for air;

the improvement in which said inhaler includes (a) a hollow cylindrical housing comprising a lower part with a lower outer diameter and an upper part, said lower part being insertable into said upper part in an axial direction and rotatable about its longitudinal axis, (b) a cylinder for containing medication which is concentrically positioned within the lower part of the housing, said cylinder comprising an outer hollow cylinder, an inner hollow cylinder with smaller outer diameter than the inner diameter of said outer hollow cylinder, so that an annular space is formed between said outer hollow cylinder and said inner hollow cylinder in which said active substance magazine can be accommodated, the inner hollow cylinder having an internal canal for flow of air and active substance and a first passage opening to said annular space, (c) said housing having an inlet opening operatively connected with said internal canal, (d) said inner hollow cylinder having an upper end, and, at said upper end, second passage openings operatively connected with said internal canal for flow of air laden with active substance, (e) means comprising a cyclone chamber operatively connected to said passage openings, (f) means providing an exit opening from said cyclone chamber, (g) means permitting axial displacement and/or rotation of the active substance magazine about its longitudinal axis, said magazine having a plurality of apertures for receiving individual doses of medication, whereby axial displacement and/or rotation of said magazine aligns successive apertures with said passage opening to said internal canal, and (h) means providing a channel for flow of air from said inlet opening to the outer wall of the outer hollow cylinder and through said outer hollow cylinder to a position in alignment with said first passage opening whereby a first air stream flows from said inlet opening through said internal canal and a second air stream expels a single dose of medication from one of said apertures, through said passage opening, into said internal canal.

2. A powder inhaler according to claim 1 in which the means permitting axial displacement and/or rotation of the active substance magazine about its longitudinal axis comprises control curves on the outer surface of said outer hollow cylinder, a ratchet furrow cylinder having groves on its inner surface, said ratchet furrow cylinder surrounding said outer hollow cylinder, and a cam follower.

3. A powder inhaler according to claim 1 in which the mouthpiece includes an outflow cylinder for air laden with active substance and there is a canal between said outflow cylinder and said upper part of the housing for flow of air around the air laden with active substance.

4. A powder inhaler according to claim 1 in which said magazine comprises a plurality of dosage disks and means are provided to interconnect said dosage disks for concurrent axial displacement and rotation.

5. A powder inhaler according to claim 4 in which the dosage disks are interconnected by cams and depressions.

6. A powder inhaler according to claim 4 in which the dosage disks are interconnected by a pin extending from one dosage disk and a bore in an adjacent dosage disk.

7. A powder inhaler according to claim 1 in which the apertures in the active substance magazine have a cross-section that becomes larger in the direction of the internal canal.

8. A powder inhaler according to claim 1 in which the means providing a channel for flow of air from said inlet opening to the outer wall of the outer hollow cylinder extends axially from above to a position adjacent the apertures in the active substance magazine.

9. A powder inhaler according to claim 1 in which the mouthpiece has a canal of a diameter that increases in the direction of the flow of the air stream.

10. A powder inhaler according to claim 1 in which each individual dose of medication is between 0.05 mg and 50 mg.

11. A powder inhaler according to claim 1 in which the amounts of biological active substances in an aperture is between 0.025 mg and 50 mg.

12. A powder inhaler according to claim 1 which has a bent mouthpiece.

13. A powder inhaler according to claim 1 in which the internal canal has a constriction in the cross-section opposite the opening.

14. A powder inhaler according to claim 1 including means for adjusting the air stream.

15. A powder inhaler according to claim 14 in which the means for adjusting the air stream comprises a valve body and an elastic membrane.

* * * * *